(12) United States Patent
Ho et al.

(10) Patent No.: US 7,690,918 B2
(45) Date of Patent: Apr. 6, 2010

(54) DENTAL IMPRESSION TRAYS

(75) Inventors: Thuy-tien Tran Ho, 11470 Foxclove Rd., Oakton, VA (US) 22124; Jose E. Walter, Ranson, WV (US)

(73) Assignee: Thuy-Tien Tran Ho, Oakton, VA (US)

(*) Notice: Subject to any disclaimer, the term of this patent is extended or adjusted under 35 U.S.C. 154(b) by 55 days.

(21) Appl. No.: 11/679,167

(22) Filed: Feb. 26, 2007

(65) Prior Publication Data

US 2007/0202457 A1   Aug. 30, 2007

Related U.S. Application Data

(63) Continuation-in-part of application No. 11/362,538, filed on Feb. 27, 2006, now abandoned.

(51) Int. Cl.
   *A61C 9/00* (2006.01)
(52) U.S. Cl. .......................................... 433/45; 433/214
(58) Field of Classification Search .............. 433/37–48, 433/71, 214
   See application file for complete search history.

(56) References Cited

U.S. PATENT DOCUMENTS

| | | | | |
|---|---|---|---|---|
| 1,652,910 A * | 12/1927 | Psayla | ........................... | 433/41 |
| 2,529,429 A * | 11/1950 | Spiro | ........................... | 433/41 |
| 4,375,965 A * | 3/1983 | Weissman | ..................... | 433/37 |
| 4,432,728 A * | 2/1984 | Skarky | ........................... | 433/37 |
| 4,445,854 A * | 5/1984 | Bekey et al. | ................... | 433/37 |
| 5,076,785 A * | 12/1991 | Tsai | .............................. | 433/46 |
| 5,336,086 A * | 8/1994 | Simmen et al. | ............... | 433/37 |
| 5,487,662 A * | 1/1996 | Kipke et al. | .................... | 433/37 |
| 5,890,895 A | 4/1999 | Tucker | | |
| 6,428,315 B1 | 8/2002 | Prestipino | | |
| 6,468,078 B2 * | 10/2002 | Guillaume et al. | ............ | 433/45 |
| 6,964,568 B1 * | 11/2005 | Segal | ........................... | 433/45 |
| 7,273,371 B2 * | 9/2007 | Massad | ........................ | 433/37 |
| 2001/0010898 A1 * | 8/2001 | Joergensen et al. | ............ | 433/45 |
| 2003/0180681 A1 * | 9/2003 | Kwon et al. | .................... | 433/45 |
| 2005/0106529 A1 * | 5/2005 | Abolfathi et al. | ............... | 433/41 |
| 2006/0166163 A1 * | 7/2006 | Ye | ................................ | 433/45 |

OTHER PUBLICATIONS www.kohler-medizintechnik.de, Wintray Kohler Implant Impression Tray, undated.
Exacta 3 in 1 Disposable Impression Trays, undated.

* cited by examiner

*Primary Examiner*—Cris L Rodriguez
*Assistant Examiner*—Hao D Mai (57) ABSTRACT

Provided are impression trays having one or more breakaway segments that allow for convenient removal of a portion of the tray, while maintaining the overall dimensions of the tray. Also provided are methods making impressions that include removing at least one breakaway segment of the provided trays. Also provided are impression trays having novel handles and trays having novel slots for the extrusion of excess impression material and retention. Further provided are kits and systems that include such impression trays.

18 Claims, 8 Drawing Sheets

FIG. 16

DENTAL IMPRESSION TRAYS

RELATED APPLICATION

This patent application is a continuation-in-part of U.S. patent application Ser. No. 11/362,538 filed on Feb. 27, 2006, now abandoned, the content and subject matter of which are hereby incorporated by reference in their entirety, including all text and figures.

FIELD

Example embodiments are generally directed to dental impression trays for holding material used to make impressions of teeth and/or gums. Example embodiments relate to impression trays that allow for impressions to be taken in various circumstances, including during procedures involving an artificial tooth root, also known as a dental implant.

BACKGROUND

When a practitioner makes an impression of a patient's teeth and/or gums, he or she places a temporarily semi-fluid composition called an "impression material" into an impression tray and inserts the tray into the patient's mouth. The practitioner maneuvers the tray within the patient's mouth relative to the patient's teeth until the desired position of the tray with respect to the teeth is achieved. The tray is maintained in this position until the impression material hardens. After the impression material has hardened enough to retain its shape, the tray is then removed from the patient's mouth. The impression may be used for example in making models of teeth for reconstruction or replacement, or the impression may be used in any other situation where a dental impression is desired.

Prior impression trays would commonly need to be drilled to obtain a hole in the tray in various procedures. Drilling holes in a tray has several disadvantages, including the creation of small particles of material that may accidentally project into the practitioner's eyes, or may be inhaled by the patient or practitioner. Additionally, the particles may contaminate a sterile environment for example, during oral surgery. Drilling holes in a tray may deform the plastic due to heat generated during the drilling and causing the bur to stall. Further, drilling holes in a tray takes a good deal of time.

One prior tray may have sections removed. But if sections are removed from that tray, the overall size may be reduced and the tray is no longer suitable for taking an impression of an entire jaw. Further, such a tray is weak and not sufficiently strong or stable for taking a suitable impression or for maintaining the dimensional accuracy of the impression as the tray is being removed from a patient after the impression material hardens.

SUMMARY

Example embodiments are generally directed to dental impression trays.

According to example embodiments, impression trays include at least one removable segment, for example a breakaway segment that may each be independently removed to create at least one opening in the tray, while maintaining the overall dimensions of the tray after one or more segments is removed. Such trays include at least one wall and a base where the at least one wall and the base are configured to be placed around at least a portion of a jaw, while retaining material from which an impression of teeth and gums in the jaw may be made. One or more breakaway segments may include for example, a portion of the base. Breakaway segments may include a portion of the base and a portion of a wall of the tray abutting the portion of the base.

Example impression trays may further include a handle, which may include one or more openings. In trays having breakaway segments, one or more openings in the handle may be aligned with at least one breakaway segment, such that if the breakaway segment is removed an opening created in the dental impression tray aligns with one or more of the openings in the handle.

Example embodiments also include impression trays that include a handle configured such that the handle has a wider portion and at least one narrower portion farther from the base than the wider portion. Such handles allow one taking a dental impression to have a better grip and may allow one to hold the tray in place better while an impression material is hardening and/or to have more leverage or more easily remove a tray from a patient's mouth after impression material has hardened.

Example embodiments also include impression trays having at least one wall, where the wall includes at least one slot adapted for extrusion of excess impression material and retention, and at least one membrane comprising an outside portion of the wall, where the membrane abuts the slot to form a pocket.

Also provided are kits and systems that include at least one such tray and optionally one or more additional components that may be useful in conjunction with such a tray, for example impression material. Such kits or systems may include for example, various trays of different sizes (for example small, medium, large, or child sizes) or configurations (for example trays for the upper or lower jaw, for one side or the other, or for the front teeth, or trays configured for differently shaped jaws). Kits or systems may include a tool adapted to assist one in removing one or more removable portions of a tray having removable portions.

Further provided are methods of making impression trays, and methods of making impressions using such trays.

BRIEF DESCRIPTION OF THE DRAWINGS

Embodiments are herein described, by way of non-limiting example, with reference to the following accompanying drawings.

DETAILED DESCRIPTION

Detailed example embodiments are disclosed herein. However, specific structural and/or functional details disclosed herein are merely representative for purposes of describing example embodiments. The claims may be embodied in many alternate forms and should not be construed as limited to only example embodiments set forth herein.

Spatially relative terms, such as "inner," "outer," "inside," "outside," "upper," "lower" and the like, may be used herein for ease of description to describe one component or feature's relationship to another component(s) or feature(s) as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting. As used herein, the singular forms "a," "an" and "the" are intended to include the plural forms as well, unless the context clearly indicates otherwise. As used herein, "another" may mean at least a second or more. It will be further understood that the terms "comprises" and/or "comprising," when used in this application, specify the presence of stated features, steps, elements, and/or components, but do not preclude the presence or addition of one or more other features, steps, elements, and/or components.

Unless otherwise defined, all terms (including technical and/or scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Reference will now be made to example embodiments, which are illustrated in the accompanying drawings, wherein like reference numerals refer to the like components throughout. Example embodiments should not be construed as limited to the particular shapes, such as the shape of the impression trays, or segments or other features thereof illustrated in the figures but are to include deviations in shapes that result, for example, from manufacturing. The figures are schematic in nature and are not intended to limit the scope of the claims.

Example embodiments are generally directed to impression trays, which include at least one wall and a base, where the at least one wall and the base are configured to be placed around at least a portion of a jaw, for example a jaw of a mammal (including humans). The trays may be configured to retain material from which an impression of teeth and gums in the jaw may be made.

Impression trays according to example embodiments include at least one removable segment, for example a breakaway segment adapted such that the segment may be independently substantially removed from the tray, such that removal of a segment creates at least one opening in the tray, while substantially maintaining the overall dimensions or configuration of the tray.

According to example embodiments, one or more breakaway segments may include for example a portion of the base. By way of non-limiting example, as depicted in FIGS. 1-6 and 11-16, various internal breakaway segments 2 may include a portion of the base 4. According to example embodiments, one or more breakaway segments 6 may include a portion of the base 4 and a portion of a wall 8 of the tray abutting the portion of the base. By way of non-limiting example, breakaway segments that include a portion of the base and a portion of the wall may be L-shaped segments that extend and wrap around from a portion of the base to the side of the impression tray. The base and wall may meet at an intersection or may be curved such that the base curves up the side to become the wall.

The segments referred to herein as "internal" are those that do not include a portion of a wall or palate plate in the breakaway segment, although they may or may not abut such portions. Although FIGS. 1-6 and 11-16 depict examples having both internal breakaway segments 2, and breakaway segments 6 that include portions of at least one wall as well as the base, it is contemplated that example trays may have one or the other type of removal segment.

Segments of the tray may be made breakaway segments, e.g., by defining such segments with weakened areas, which may include for example, thinner portions of tray material, notches, or openings such as slits or holes, positioned with respect to a desired breakaway portion to allow a practitioner to be able to substantially breakaway that portion from the tray. According to example embodiments, openings such as slits or holes of various sizes in the base may create weakened portions in the base to define breakaway segments. Additionally, thicker portions of tray material, such as ribs 30 (see e.g., FIGS. 4 and 14), may further define removable segments. Ribs 30 may also be used to provide added strength, stability or rigidity to the tray. Ribs may be configured such that they can break in desired locations as well, for example by adding notches to the ribs.

According to example embodiments, breakaway segments do not span the width of the base from the outer wall to the palatal plate or inner wall and do not have weakened portions at intersections of the base and wall. That is, according to example embodiments, segments do not breakaway at intersections of the base and the wall(s). Rather, breakaway segments of the base abutting a wall, include a portion of the wall.

By way of further example, breakaway segments may be further segmented into smaller breakaway segments.

Dental impression trays provided herein may further include a handle, which may include one or more openings. By way of non-limiting example, as shown e.g., in FIG. 2, a handle 10 may have one or more openings 12. In trays having breakaway segments, one or more openings in the handle may be aligned with at least one breakaway segment 14, such that if the breakaway segment is removed, an opening created in the dental impression tray aligns with one or more of the openings in the handle. Such embodiments may be useful for example, where a post may be extending from the front of the jaw such that the handle of a dental impression tray might otherwise get in the way, even if other portions of the tray are removed.

According to example embodiments, impression trays may include an outer wall 16. One or more breakaway segments may include a portion of the base and a portion of the outer wall abutting the portion of the base. Further examples (such as the example depicted in FIGS. 1-6) may include a palatal plate 18 (for example for certain trays adapted for use with the upper jaw). Alternative examples may include an inner wall 56 (such as the example depicted in FIGS. 11-16), which may be used for either the upper jaw or the lower jaw. In embodiments having an inner wall 56, one or more breakaway segments may include a portion of the base and a portion of the inner wall abutting the portion of the base.

When one or more breakaway segments are removed, the overall dimensions of the tray remain the same. That is, a hole is created in the tray, as opposed to breaking off a portion of the tray.

Example trays provided herein may include one or more retention structures 20 (see e.g., FIG. 2) extending upwardly from said base. Although such retention structures 20 are depicted in the Figures in the shapes of "X's" and "O's", it is contemplated that any suitable shape may be used.

Dental impression trays provided herein may include any suitable material for such trays known to those skilled in the art. By way of non-limiting example, impression trays may be formed using a polymer composition. Suitable polymer compositions may include, but are not limited to, one or more of ABS, polycarbonate, nylon or any other composition known by those in the art. By way of non-limiting example, substantially clear polymers may be used, which may be useful for example, in allowing a practitioner to visualize the teeth and any pins, posts or other devices. Visualization may help one determine for example, which, if any, portion of a tray to remove before inserting impression material to the tray. According to example embodiments, translucent and/or opaque material may be used. Trays provided herein may include at least one composition selected from the group consisting of substantially clear, translucent, and opaque compositions.

According to non-limiting example embodiments, trays may be disposable trays.

Dental impression trays may be adapted in many different configurations. According to example embodiments, trays may be configured for use with an upper or lower jaw. It is also contemplated however, that trays may be configured for use with both jaws as shown for example in FIGS. 9 and 10. Alternatively, trays may be configured for use only on one side of a jaw (e.g., the right or left). According to other embodiments, impression trays may be configured for use in a front portion of a jaw. Such embodiments that are configured to take an impression of desired teeth and/or gums, may be advantageous for example in not requiring the use of excess impression material. Embodiments configured for use in a front portion of a jaw may also be useful with respect to fitting a tray to a patient, because it is easier to fit only the front portion of a jaw than the entire jaw, which may have many different sizes and shapes.

Example embodiments also include impression trays that include a handle configured such that the handle has a wider portion and at least one narrower portion further from the base than the wider portion. Such handles allow one taking a dental impression to have a better grip and may allow one to hold the tray in place better while an impression material is hardening and/or to have more leverage or more easily remove a tray from a patient's mouth after impression material has hardened.

According to a non-limiting example, a handle may be configured such that a width of the handle at a location one-quarter the distance from the end of the handle is less than two-thirds the width of the handle at its widest location. In particular, such a handle may allow one to hold the tray in place better while an impression material is hardening and/or to have more leverage or more easily remove a tray from a patient's mouth (e.g., by virtue of increased area of the handle) after impression material has hardened. Other distances and other relative handle widths are also included, which have a wider portion and a narrower portion.

Figure 3:
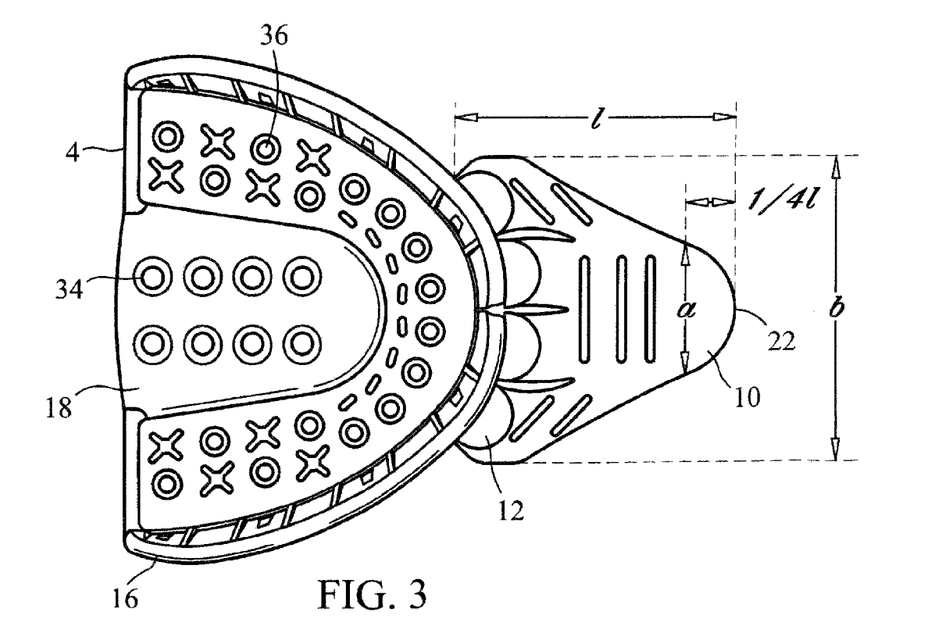
FIG. 3 is a top view of the impression tray of FIGS. 1-2 in accordance with non-limiting example embodiments.
Figure 13:
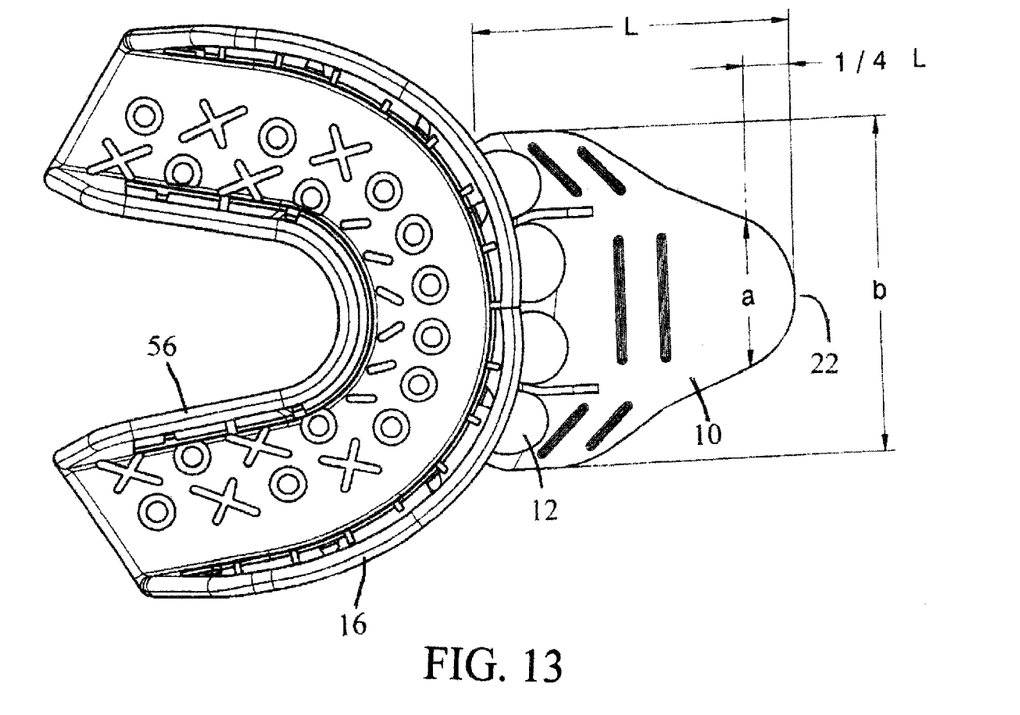
FIG. 13 is a top view of the impression tray of FIGS. 11-12 in accordance with non-limiting example embodiments.

By way of non-limiting example, FIGS. 3 and 13 depict trays having example handles. As shown in FIGS. 3 and 13, the handle 10 has a width "a" at a location one-quarter the length of the handle "l" from the end of the handle 22, where width "a" is less than ⅔ a width "b" at the handle's widest location. FIGS. 3 and 13 depict the handle narrowing at a location closer to the base of the tray, but such narrowing is not necessary. FIGS. 3 and 13 also depict the handle as part of a dental impression tray that includes at least one removable segment as described herein. This is by way of example only. It is contemplated that handles that have a widened portion may be used in conjunction with any impression tray, not just those having breakaway segments.

Example embodiments also include impression trays having at least one opening adapted for extrusion of excess impression material from the tray, which impression material may grip or lock to the outside of the tray and provide improved retention. When the impression material locks to the tray, the impression material is secured to the tray and assists in removal of the tray from the patient's mouth after the impression material hardens.

Non-limiting example embodiments, include impression trays having at least one wall, where the wall includes at least one slot adapted for extrusion of excess impression material and retention. The wall further includes at least one membrane comprising an outside portion of the wall (with respect to where a patient's teeth would be located within an inside portion of the tray), where the membrane abuts the slot to form at least one pocket for excess impression material. The membrane may include for example, a portion of the outside part of the wall cut less than all the way through the wall. The slot, which extends from the inside portion of the wall all the way through the wall, may be of any suitable size or shape to allow for extrusion of excess impression material from the tray. A vertical slot for example, may better retain the impression material, so the impression material does not pull away or move side to side or up and down and deform the mold.

According to example embodiments, the at least one wall that includes one or more slots, may be an outer wall of the impression tray. According to example embodiments, the slot(s) are included on an inner wall of the tray. Some embodiments having both outer and inner walls may include one or more slots in each.

Figure 4:
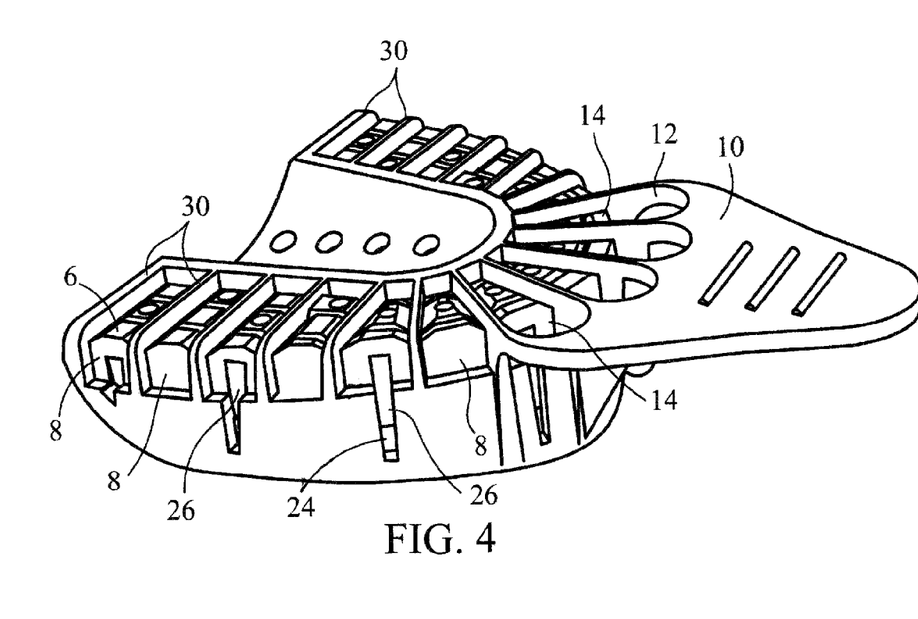
FIG. 4 is a perspective view including a side/bottom of the impression tray of FIGS. 1-3 in accordance with non-limiting example embodiments.

An example of at least one slot adapted for extrusion of excess impression material is depicted e.g., in FIG. 4. As shown in FIG. 4, a membrane 24 comprising an outside portion of the wall (with respect to where a patient's teeth would be located within an inside portion of the tray) abutting a slot 26 forms at least one pocket for retention of impression material. FIG. 4 depicts slots in an outer wall of a tray. However, embodiments having an inner wall, such as a tray configured for a lower jaw, may alternatively or additionally have slots in the inner wall as shown for example in FIG. 14.

Figure 14:
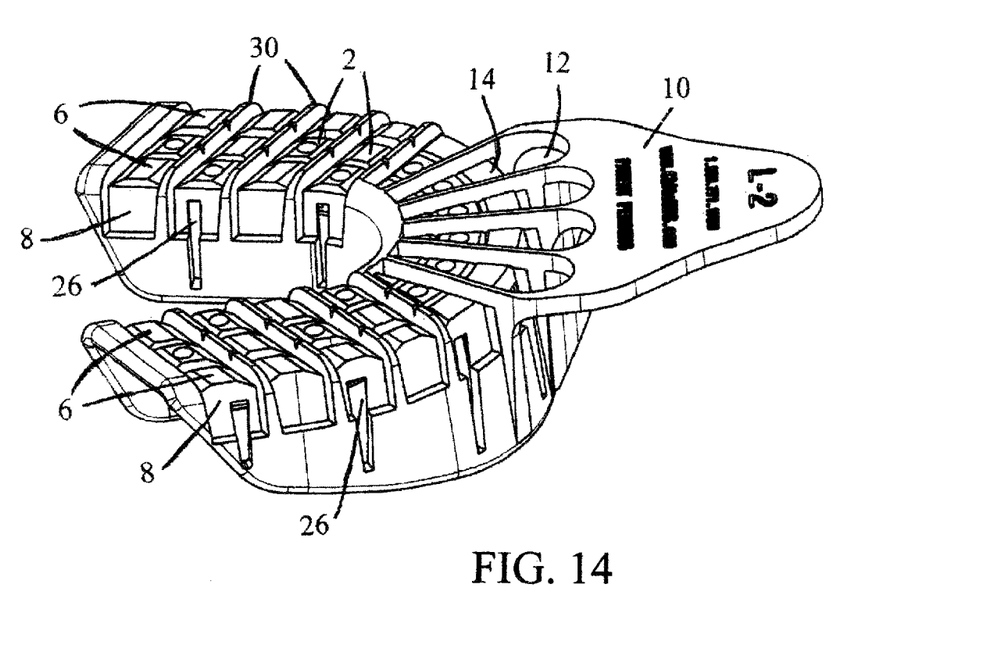
FIG. 14 is a perspective view including a side/bottom of the impression tray of FIGS. 11-13 in accordance with non-limiting example embodiments.

While FIGS. 4 and 14 depict the slots as part of an impression tray that includes at least one removable segment as described herein, this is by way of example only. It is contemplated that the described slots may be used in conjunction with other types of impression trays that do not necessarily have breakaway segments.

Trays having at least one breakaway segment may be adaptable for use in situations where a structure may interfere with taking a dental impression using conventional trays, for example, when an impression is to be made on a dental implant where a post from a pick up impression coping is extending beyond the base of the tray. Trays may eliminate unnecessary steps, reduce time, or cost and enhance the standard of treatment. Trays provided herein may be used for any purpose known by those skilled in the art.

Also provided are methods of making dental impression trays described herein. In particular, dental trays having configurations for example those described herein may be made by those skilled in the art by methods commonly used in the art depending for example on the materials used.

Example embodiments also include methods of making dental impressions using trays as described herein. By way of non-limiting example, a method of making a dental impression using a dental impression tray having at least one removable segment may include removing at least one breakaway segment from such a dental impression tray, inserting impression material to the dental impression tray, positioning the dental impression tray with respect to teeth of a patient, allowing impression material to substantially harden, and removing the dental impression tray from the teeth of the patient. According to some embodiments, methods may include fitting a tray in a patient's mouth, determining which, if any, breakaway segments should be removed, and other steps that would be apparent in view of this disclosure.

Also provided are kits and systems that include at least one such tray and optionally one or more additional components that may be useful in conjunction with such a tray, for example impression material. Such kits or systems may include for example, various trays of different sizes (for example small, medium, large, or child sizes) and/or configurations (for example trays for the upper or lower jaw, for one side or the other, or for the front teeth, or trays configured for differently shaped jaws). It may be useful for one who makes dental impressions to have a kit containing one or more trays of different sizes or for different portions of the mouth, such that the appropriate tray is readily available, regardless of the patient's mouth size or shape, or the desired portion of the mouth for which an impression is desired. As some trays are used, such a kit may be replenished for example by purchasing individual trays or groupings of trays.

According to example embodiments in which the tray has at least one removable segment, kits or systems may include a tool adapted to assist one in removing one or more removable portions of the tray. For example a punch tool or other tool may be included in such kits or systems for removing one or more segment(s) of the tray. In addition, a file may be included in the kit or system to remove any uneven or otherwise undesired portions of the tray after removal of the segment(s). The file may be separate from, or part of, the tool for removing a segment of the tray.

According to example embodiments, kits or systems may include one or more types of impression material for use with trays provided in the kit. Suitable impression materials are known to those skilled in the art. Further provided may be other materials that may be used in taking an impression, for example a bonding agent may be included in the kit.

Devices, methods, kits and systems provided herein may be modified as would be apparent to those skilled in the art. Such modifications are within the scope of the present invention. By way of non-limiting example, as discussed above, devices may be designed for different jaw sizes, for different purposes (for example making an impression of certain teeth or certain portions of the jaw) and/or for different materials to be used in such devices, and are not intended to be limited to the specific examples set forth hereinabove or in the examples provided below. Thus, the following examples are meant to be illustrative and should not in any way serve to limit the scope of the claims. As would be apparent to skilled artisans, various changes and modifications are possible and are contemplated and may be made by persons skilled in the art.

Example 1

In this example, embodiments are depicted in FIGS. 1-6 in which a dental impression tray having removable segments is provided for an upper jaw. The dental impression tray has a base 4, and an outer wall 16, wherein the base and outer wall are configured to be placed around an upper jaw of a patient, while retaining impression material therein. The depicted tray has a palatal plate 18, which, along with the base and outer wall define the space in which impression material is maintained.

As shown in FIGS. 1-6, the removable segments may include segments 2 in a portion of the base 4 and/or segments 6, which include a portion of the base and a portion 8 of at least one wall of the tray. As depicted in FIGS. 1-6, these embodiments include both internal breakaway segments and breakaway segments that include a portion of an outer wall.

Figure 5:
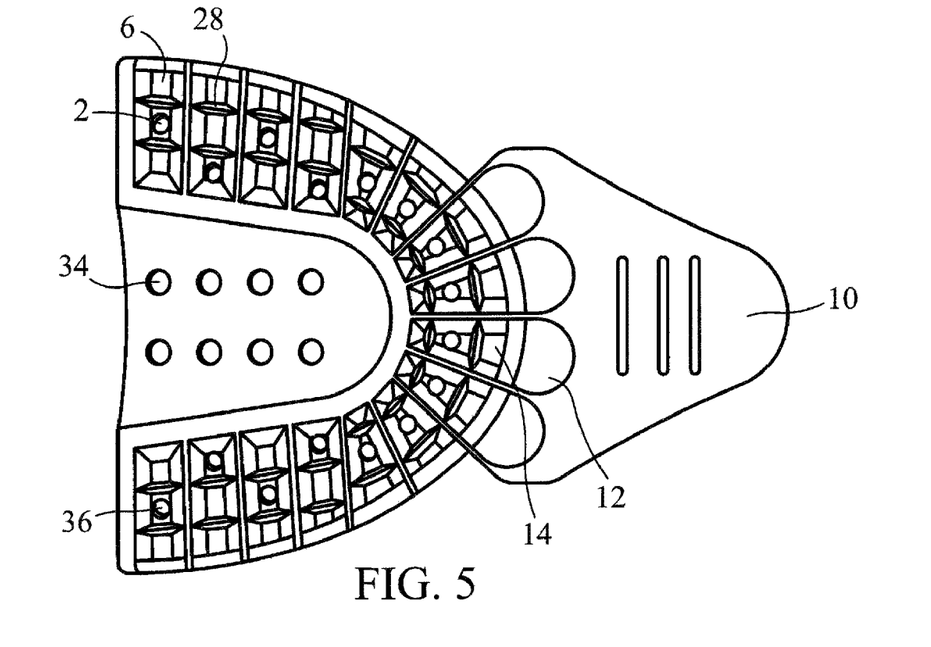
FIG. 5 is a bottom view of a bottom of the impression tray of FIGS. 1-4 in accordance with non-limiting example embodiments.
Figure 6:
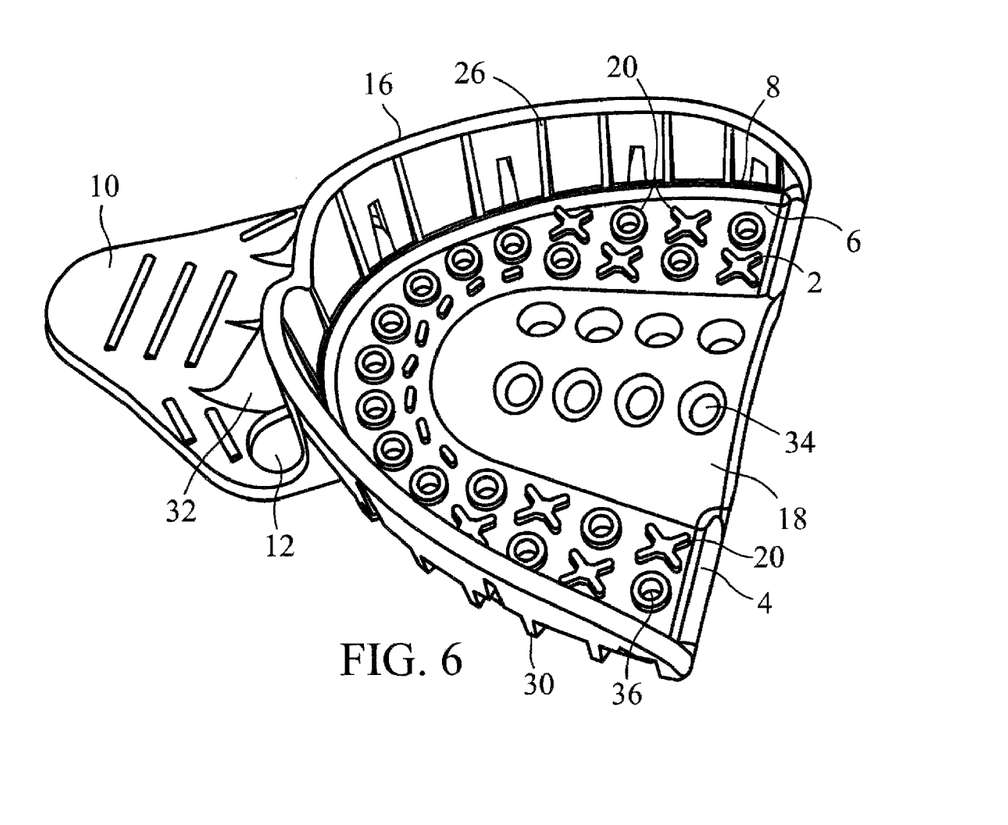
FIG. 6 is a perspective view of a top of the impression tray of FIGS. 1-5 in accordance with non-limiting example embodiments.

As depicted for example in FIG. 5, segments of the tray may be made breakaway segments, e.g., by defining such segments with weakened areas 28 and/or other thinner portions of tray material and/or openings, such as holes or slits, around a desired breakaway portion. Additionally, thicker portions of tray material, for example ribs 30 (see e.g., FIG. 4), may further define removable segments. The ribs themselves may break at desired locations, for example, by having weakened portions such as notches in the ribs. As shown for example in FIG. 4, for breakaway segments 6 that include portions of a wall 8, the portions of the wall that are intended to be able to break away may be for example, thinner than other portions of the wall, and may be further defined by holes in the wall, slits and/or thicker portions of wall to allow each segment to be substantially broken away from the remainder of the tray without breaking away unintended segments and without affecting the structural integrity of the tray.

The depicted example trays include one or more retention structures 20 extending upwardly from said base. The retention structures 20 are depicted in FIGS. 1-6 as "X's" and "O's." According to these examples, each retention structure is positioned within a removable segment, such that each retention structure does not extend across multiple removable segments thereby potentially hindering the ability of a segment to be removed.

Dental impression trays according to the examples depicted in FIGS. 1-6 include a handle 10 having four openings 12 positioned with respect to four corresponding breakaway segments 14, such that an opening created by removal of a breakaway segment aligns with an opening in the handle. The shape, size and/or number of openings in the handle and/or of breakaway segments may be determined for example, based on the relative size, shape and configuration of expected posts or other protrusions and the amount of open area generally desired around such posts or protrusions, such that the posts or protrusions do not significantly contact the tray.

Figure 1:
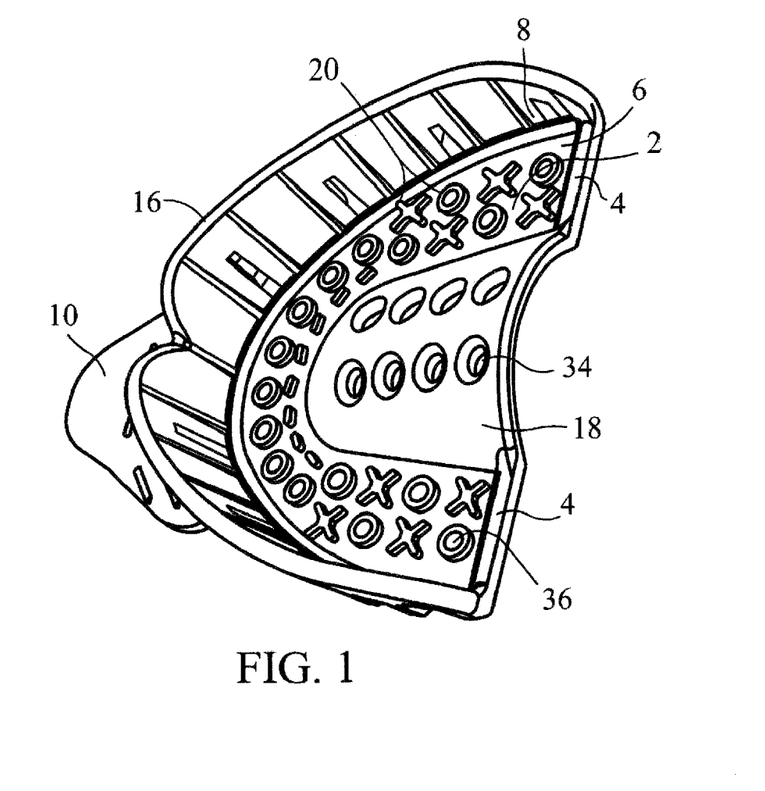
FIG. 1 is a perspective view of a top of an impression tray in accordance with non-limiting example embodiments.
Figure 2:
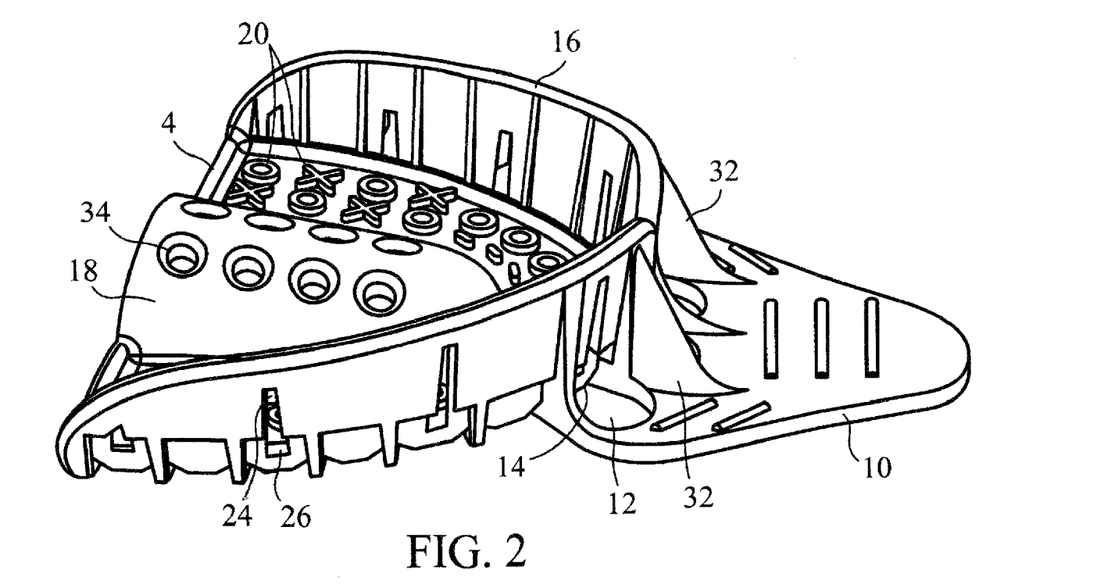
FIG. 2 is a perspective view including a side/top of the impression tray of FIG. 1 in accordance with non-limiting example embodiments.

The handle may be configured for increased strength, structural integrity and other desired characteristics. For example, as shown in FIG. 2, one or more reinforcing pieces 32 may be located between or around openings in the handle. Further, the shape of the handle may be configured for added strength and/or stability. By way of non-limiting example, as depicted in FIGS. 1-6, the handle has a wider portion closer to the base, and has narrower portions tapering to the end 22 away from the base of the tray. Such a shape having a widened portion and a narrower portion may allow one taking a dental impression to have a better grip of the tray, provides a finger rest, and provides more leverage in removal of a tray from a patient's mouth.

The tray depicted in FIGS. 1-6 is a disposable tray comprising a substantially clear polymer composition. A non-limiting example of a polymer composition may include polycarbonate. Trays provided herein are not limited to polymers, however, and need not be substantially clear compositions. Trays may include one or more translucent or opaque materials.

The example embodiments depicted in FIGS. 1-6 include multiple slots 26 in an outer wall 16 adapted for extrusion of excess impression material from the tray. A membrane of the outside portion of the wall (24, as shown in FIGS. 2 and 4), extends beyond the slot 26 to form at least one pocket for excess impression material. The pockets on the outside portion of the outer wall include a thinner membrane portion 24 of an outside portion of the wall abutting and extending beyond a slot created in the inside portion of the wall.

According to this example, the palatal plate 18 includes multiple openings 34, which also provide for extrusion of excess impression material and retention. Openings 36 in the base of the tray may further provide locations for extrusion of excess impression material and retention. The size, shape and configuration of openings in the base and palatal plate are not intended to be limited to those depicted herein.

Example 2

Figure 7:
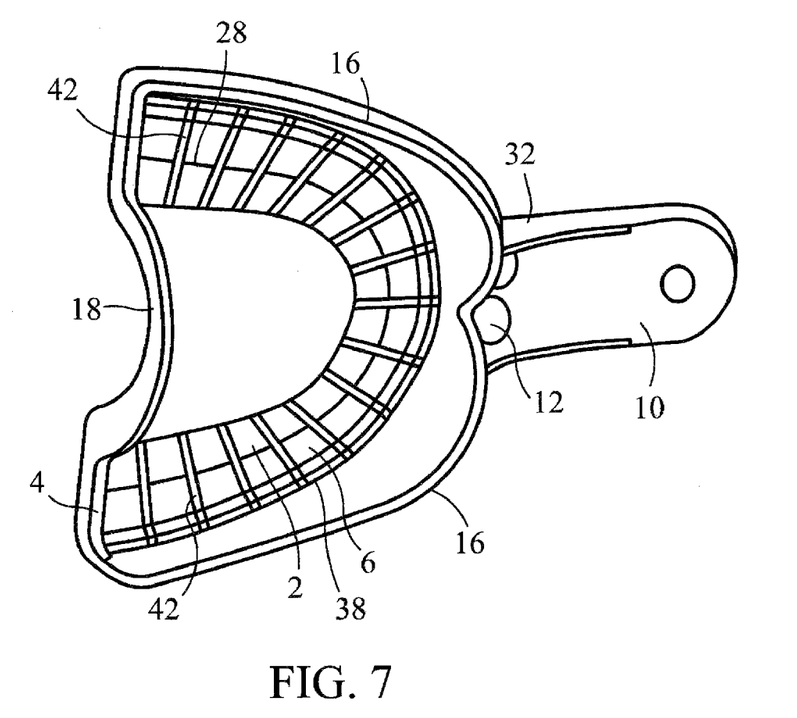
FIG. 7 is a view of the top of an impression tray according to non-limiting example embodiments, showing the portion of the tray that holds the impression material.
Figure 8:
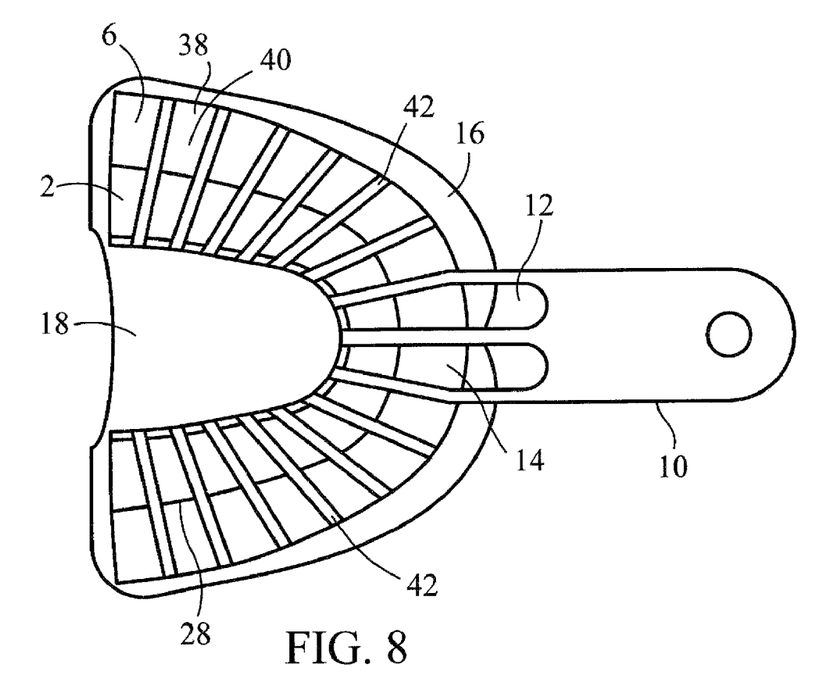
FIG. 8 is a bottom view of the tray of FIG. 7.

FIGS. 7 and 8 depict other example embodiments of dental impression trays having removable segments, in accordance with non-limiting embodiments. FIG. 7 shows an impression tray for an upper jaw from the aspect onto which the impression material is placed. FIG. 8 is a bottom view (impression material would be on the side away from the viewer) of the tray. As in the previous example, the dental impression tray has a base 4, and an outer wall 16, wherein the base and outer wall are configured to be placed around an upper jaw, while retaining impression material therein. The depicted tray has a palatal plate 18, which along with the base and outer wall define the space in which impression material is maintained.

As shown in FIGS. 7 and 8, breakaway segments may include segments 2 and 6 which include a portion of the base and optionally include a portion of a wall abutting the base. The area defined by the wall abutting the base, may simply be a curved section 38 as depicted in FIGS. 7 and 8 with no defined corner or actual intersection point or line. In such embodiments, segments that include a portion of the base and a portion of the wall may be one continuous segment having a curved portion 38 and a substantially flat portion 40. In such embodiments, the curved portion 38 may be breakably attached to a portion of the wall. By way of non-limiting example, the tray may be one continuous material with the breakaway segment being made of thinner material than the wall, or a thinner portion of the material may separate the breakaway segment from the remainder of the wall.

As depicted in FIGS. 7 and 8, segments of the tray may be made breakaway segments, by defining such segments with e.g., perforations, slits, notches, spaces, indentations or other weakened areas 28 and/or other thinner portions of tray material and/or openings such as holes or slits around a desired breakaway portion or thicker portions of tray material around any desired breakaway portion. According to example embodiments ribs 42 may be used to separate breakaway segments from one another. Example ribs 42 may extend for example, from an outer wall to an inner wall, or in the embodiments depicted in FIGS. 7 and 8 such ribs 42 may extend from the outer wall 16 to the palatal plate 18. The ribs themselves may break at desired locations, for example, by having weakened portions such as notches in the ribs.

Dental impression trays according to the examples depicted in FIGS. 7 and 8 include a handle 10 having two openings 12 positioned with respect to corresponding breakaway segments 14, such that an opening created by removal of a breakaway segment aligns with an opening in the handle. The shape and size of the openings may be determined for example, based on the relative size, shape and configuration of expected posts or other protrusions and/or the amount of open area generally desired around such posts or protrusions, such that they preferably do not contact the tray.

The handle may be configured for increased strength, structural integrity and other desired characteristics. For example, as shown in FIG. 7, one or more reinforcing pieces 32 may be located around the openings.

Example 3

Figure 9:
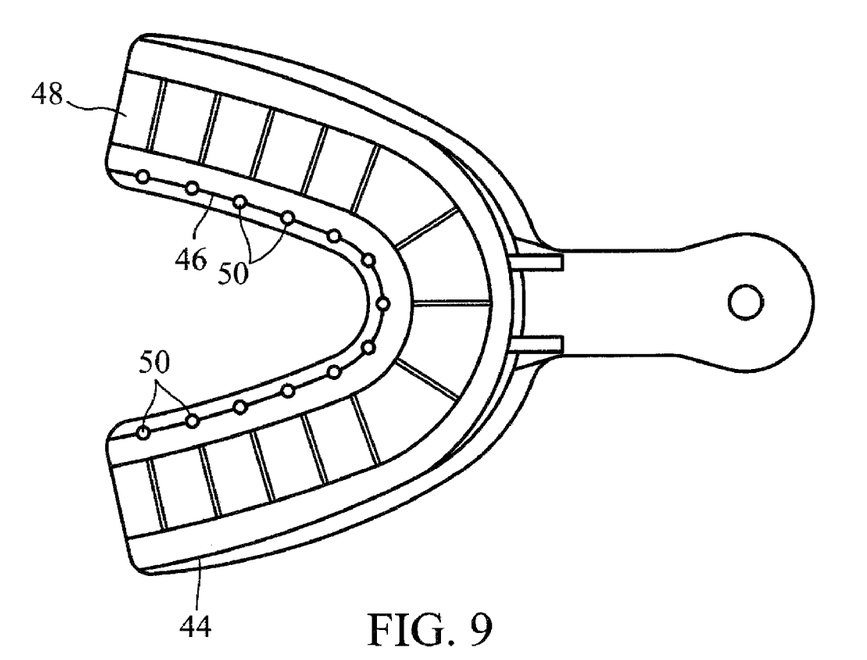
FIG. 9 shows a top planar view of an impression tray according to non-limiting example embodiments.
Figure 10:
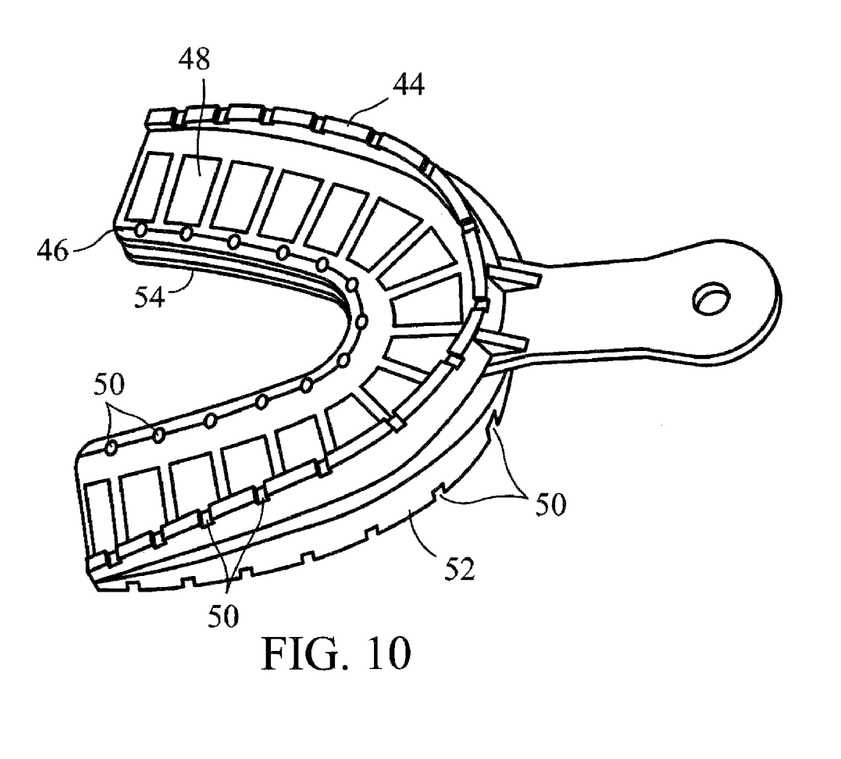
FIG. 10 shows a perspective view of the tray of FIG. 9.
Figure 11:
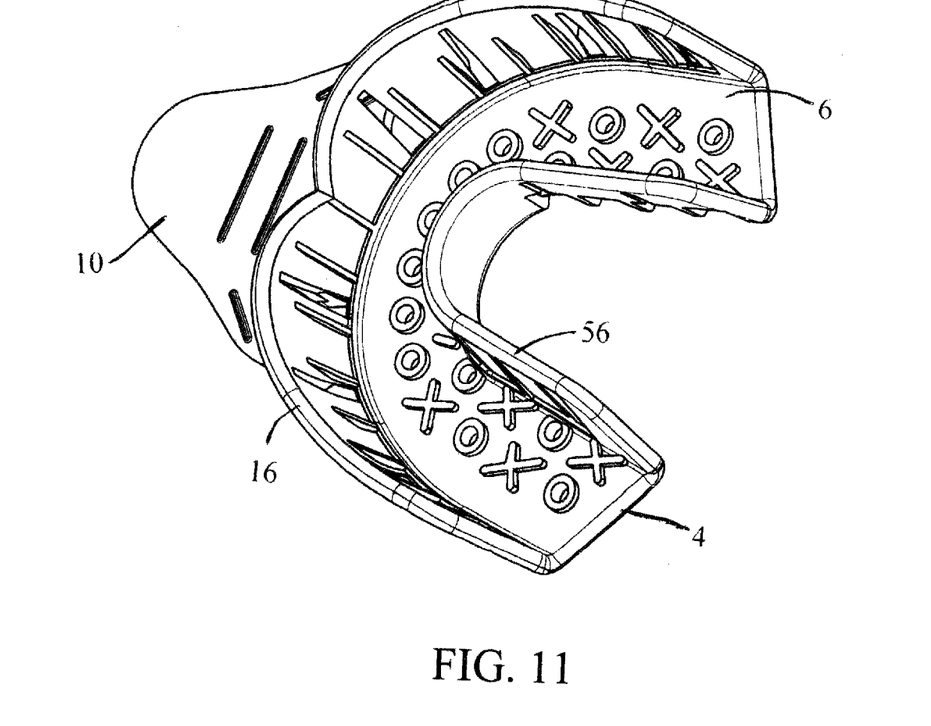
FIG. 11 is a perspective view of a top of an impression tray in accordance with non-limiting example embodiments.

In this example, embodiments of impression trays are depicted in FIGS. 9 and 10 in which an impression of both upper and lower teeth may be taken at one time. Such embodiments may be useful for example, in providing information relating to occlusal relationships. Embodiments according to this example have opposing outer 44 and inner 46 walls and a segmented base 48, which define a space in which impression material may be added. The segmented base allows for certain desired segments to be removed from the tray, while maintaining the overall structure of the tray, which may allow for example, a post to extend through the removed segment(s). Although the segments depicted in FIGS. 9 and 11 primarily include portions of the base, it is contemplated that parts of either wall may also be included in one or more such segments.

One or more openings may be included in such impression trays to permit extrusion of excess impression material. For example, openings such as notches 50 at the top of the outer and/or inner wall (or for the bottom jaw, at the bottom of the outer and/or inner wall) may allow for extrusion of impression material from the tray and may also provide a location in which impression material may harden to assist in holding the impression material in place.

As shown in FIG. 10, in these embodiments, an outer wall 44 extends upward for a portion of the tray designed for an upper jaw, and an outer wall 52 extends downward for a portion of the tray adapted for a lower jaw. Similarly, portions of an inner wall extend both upward 46 and downward 54 corresponding to each jaw.

Although the invention has been described in example embodiments, many additional modifications and variations would be apparent to those skilled in the art.

Example 4

In this example, embodiments are depicted in FIGS. 11-16 in which a dental impression tray having removable segments is provided for a lower or upper jaw. The dental impression tray has a base 4, an outer wall 16, and an inner wall 56, wherein the base and walls are configured to be placed around a jaw of a patient, while retaining impression material therein. The base and walls define the space in which impression material is maintained.

As shown in FIGS. 11-16, the removable segments may include segments 2 in a portion of the base 4 and/or segments 6, which include a portion of the base and a portion 8 of at least one wall of the tray. As depicted in FIGS. 11-16, these embodiments include both internal breakaway segments 2 and breakaway segments 6 that include a portion of an outer or inner wall 8.

Figure 15:
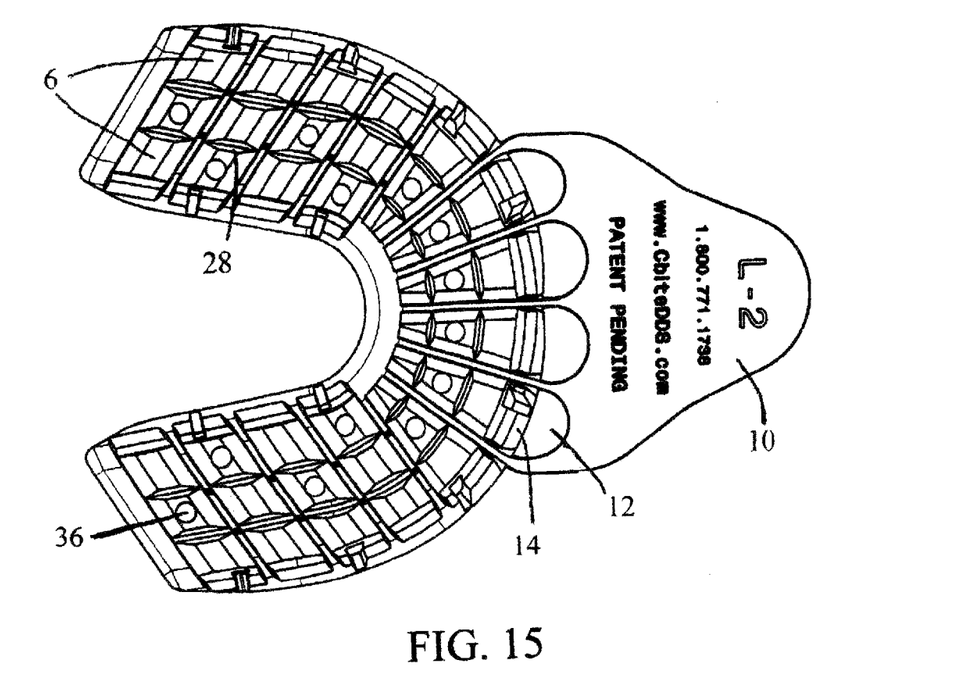
FIG. 15 is a bottom view of a bottom of the impression tray of FIGS. 11-14 in accordance with non-limiting example embodiments.
Figure 16:
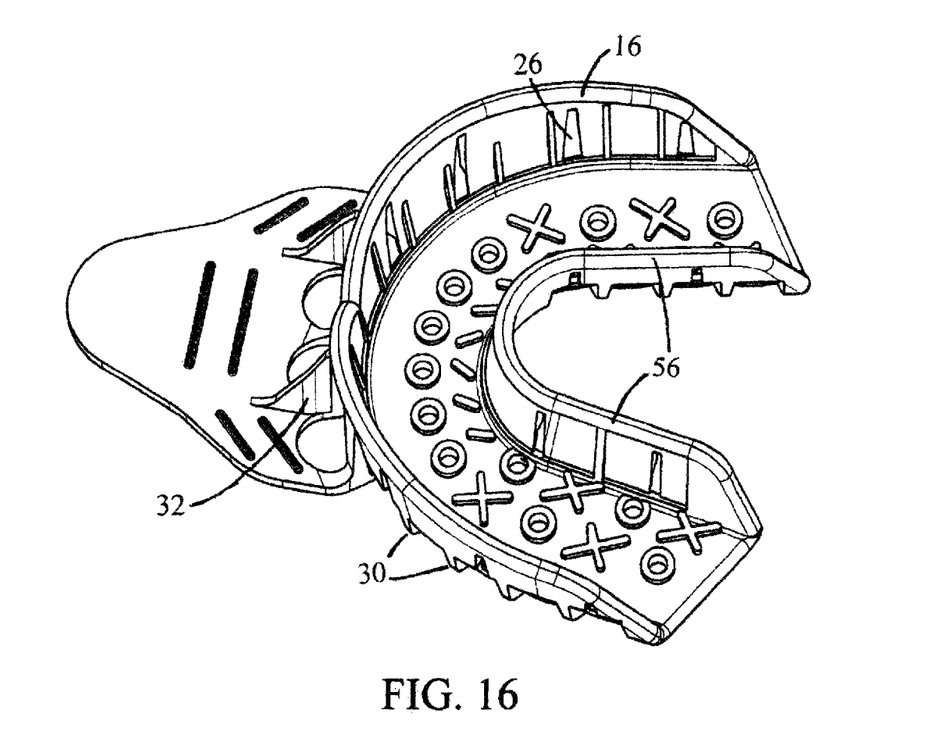
FIG. 16 is a perspective view of a top of the impression tray of FIGS. 11-15 in accordance with non-limiting example embodiments.

As depicted for example in FIG. 15, segments of the tray may be made breakaway segments, e.g., by defining such segments with weakened areas 28 and/or other thinner portions of tray material and/or openings, such as holes or slits, around a desired breakaway portion. Additionally, thicker portions of tray material, for example ribs 30 (see e.g., FIG. 14), may further define removable segments. The ribs themselves may break at desired locations, for example, by having weakened portions such as notches in the ribs. As shown for example in FIG. 14, for breakaway segments 6 that include portions of a wall 8, the portions of the wall that are intended to be able to break away may be for example, thinner than other portions of the wall, and may be further defined by holes in the wall, slits and/or thicker portions of wall to allow each segment to be substantially broken away from the remainder of the tray without breaking away unintended segments and without affecting the structural integrity of the tray.

Figure 12:
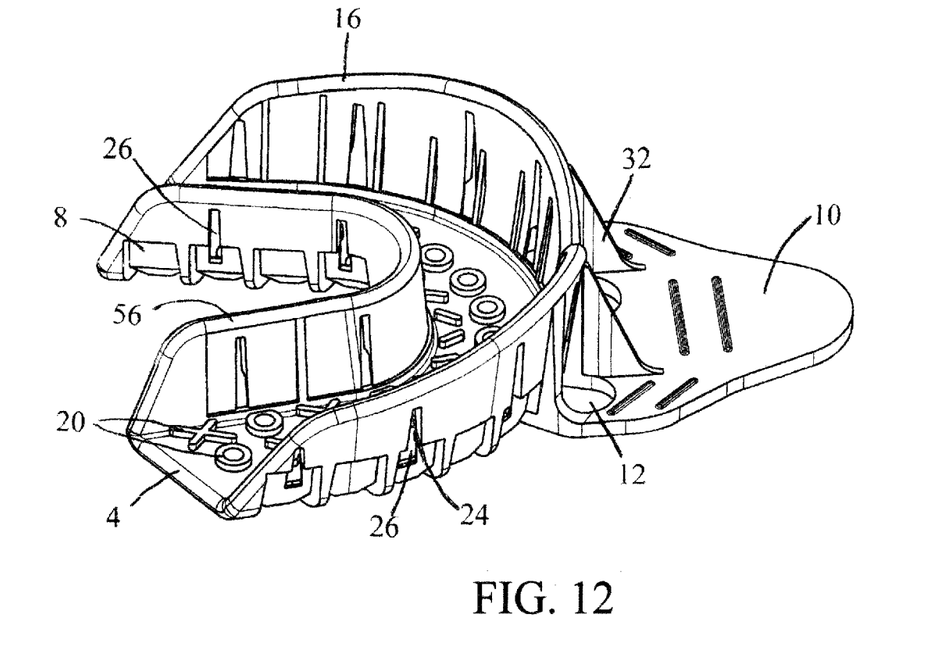
FIG. 12 is a perspective view including a side/top of the impression tray of FIG. 11 in accordance with non-limiting example embodiments.

The depicted example trays include one or more retention structures 20 extending upwardly from said base (see e.g., FIG. 12). The retention structures 20 are depicted in FIGS. 1-6 as "X's" and "O's." According to these examples, each retention structure is positioned within a removable segment, such that each retention structure does not extend across multiple removable segments thereby potentially hindering the ability of a segment to be removed.

Dental impression trays according to the examples depicted in FIGS. 11-16 include a handle 10 having four openings 12 positioned with respect to four corresponding breakaway segments 14, such that an opening created by removal of a breakaway segment aligns with an opening in the handle. The shape, size, and/or number of openings in the handle and/or of breakaway segments may be determined based on the relative size, shape and configuration of expected posts or other protrusions and the amount of open area generally desired around such posts or protrusions, such that the posts or protrusions do not significantly contact the tray.

The handle may be configured for increased strength, structural integrity and other desired characteristics. For example, as shown in FIG. 12, one or more reinforcing pieces 32 may be located between or around openings in the handle. Further, the shape of the handle may be configured for added strength and/or stability. By way of non-limiting example, as depicted in FIG. 13, the handle has a wider portion closer to the base, and tapers to the end 22 away from the base of the tray. Such a shape having a widened portion may allow one taking a dental impression to have a better grip of the tray, provides a finger rest, and provides more leverage in removal of a tray from a patient's mouth.

The tray depicted in FIGS. 11-16 is a disposable tray comprising a substantially clear polymer composition. A non-limiting example of a polymer composition may include polycarbonate. As indicated above, trays are not limited to substantially clear polymer compositions.

The example embodiments depicted in FIGS. 11-16 include multiple slots 26 in an outer wall 16 and/or in an inner wall 56, which slots are adapted for extrusion of excess impression material from the tray. A membrane of the outside portion of the wall (24, as shown e.g., in FIG. 12), extends beyond the slot 26 to form at least one pocket for excess impression material. The pockets on the outside portion of the outer wall include a thinner membrane portion 24 of an outside portion of the wall abutting and extending beyond slots created in the inside portion of the wall.

According to this example, openings 36 in the base of the tray may provide locations for extrusion of excess impression material and retention. The size, shape and configuration of openings in the base are not intended to be limited to those depicted herein.

What is claimed is:

1. An impression tray comprising:
   at least one wall and a base configured to be placed around at least a portion of a jaw while retaining impression material;
   a plurality of segments comprising at least one breakaway segment, said at least one breakaway segment configured to be independently removable from the impression tray by breaking along weakened areas, such that removal of said at least one breakaway segment creates an opening in the base and/or in the wall of said impression tray, while maintaining the dimensions of said impression tray; and
   a handle having at least one opening, wherein said at least one opening in the handle is aligned with said at least one breakaway segment; wherein a common opening is formed of said at least one opening in the handle and said opening in the base and/or in the wall when said at least one of breakaway segment is removed, wherein the common opening allows a post or other protrusion from the jaw to extend through the common opening without significantly contacting the impression tray.

2. The impression tray of claim 1 further configured for an upper jaw having a palatal plate.

3. The impression tray of claim 1 further configured for a lower jaw having an outer wall and an inner wall.

4. The impression tray of claim 1 further made of clear or translucent material.

5. The impression tray of claim 1 further having one or more retention structures for retention and stabilization of impression material.

6. The impression tray of claim 1 further configured for one side of the jaw.

7. The impression tray of claim 1 further configured for making an impression of the front teeth.

8. The impression tray of claim 1 wherein said wall has at least one slot configured to allow extrusion of impression material and a membrane abutting said at least one slot to assist in retention of impression material; and
   one or more ribs, each of said one or more ribs defines at least a portion of at least one breakaway segment; each of said one or more ribs also provide added strength and rigidity to the impression tray.

9. An impression tray comprising:

at least one wall and a base configured to be placed around at least a portion of a jaw while retaining impression material;

at least two breakaway segments which break at a weakened area, each of said breakaway segments comprises a portion of the base and a portion of the wall abutting said base, wherein removal one of said at least two breakaway segments creates an opening in the wall and/or in the base; and a handle having at least two openings, wherein at least one of said at least two openings in the handle is aligned with at least one of said at least two breakaway segments; wherein a common opening is formed of said at least one of said at least two openings in the handle and said opening in the base and/or in the wall when said at least one of said at least two breakaway segments is removed, wherein the common opening allows a post or other protrusion from the jaw to extend through said common opening without significantly contacting the impression tray.

10. The impression tray of claim 9 wherein the handle is wider at the end proximal to the impression tray and narrows toward portion of said handle distal from said impression tray.

11. An impression tray comprising:

at least one wall and a base for retaining impression material;

a plurality of breakaway segments, wherein removal one of the plurality of breakaway segments creates an opening in the base and/or in the wall; and a handle having at least two openings, wherein said at least two openings in the handle are aligned with at least two of said plurality of breakaway segments;

wherein a common opening is formed of one of said at least two openings in the handle and said opening in the wall and/or in the base when one of said plurality of breakaway segments is removed, wherein the common opening allows a post or other protrusion from the jaw to extend through the common opening without significantly contacting the impression tray.

12. The impression tray of claim 11 further configured for an upper jaw having a palatal plate.

13. The impression tray of claim 11 further configured for a lower jaw having an outer wall and an inner wall.

14. The impression tray of claim 11 further made of clear or translucent material.

15. The impression tray of claim 11 further having one or more retention structures for retention and stabilization of impression material.

16. The impression tray of claim 11 further configured for one side of the jaw.

17. The impression tray of claim 11 further configured for making an impression of the front teeth.

18. The impression tray of claim 11 wherein said wall has at least one slot configured to allow extrusion of impression material and a membrane abutting said at least one slot to assist in retention of impression material; and one or more ribs, each of said one or more ribs separate breakaway segments from one another; said one of more ribs also provide added strength and rigidity to the impression tray.

\* \* \* \* \*